United States Patent [19]

MacCleary et al.

[11] 4,182,959
[45] Jan. 8, 1980

[54] METHODS FOR USE IN FIRE INVESTIGATION

[75] Inventors: Randall C. MacCleary; Ronald N. Thaman, both of Worthington, Ohio

[73] Assignee: SEA Investigation Division, Inc., Columbus, Ohio

[21] Appl. No.: 928,527

[22] Filed: Jul. 27, 1978

[51] Int. Cl.² .......................................... A61K 27/02
[52] U.S. Cl. .............................. 250/492 R; 250/310; 324/71 EB
[58] Field of Search ........... 250/305, 272, 310, 412 R, 250/306, 307; 324/67, 71 EB

[56] References Cited

U.S. PATENT DOCUMENTS

| | | | |
|---|---|---|---|
| 2,418,029 | 3/1947 | Hillier | 250/310 |
| 2,982,814 | 5/1961 | Fine | 250/310 |
| 4,134,014 | 1/1979 | Neave et al. | 250/310 |

*Primary Examiner*—Harold A. Dixon
*Attorney, Agent, or Firm*—Frank H. Foster

[57] ABSTRACT

A method for testing whether an excessively high electrical current caused or was caused by a fire. A melt bead from an electrical conductor is selected from the region of a fire. Its relative oxygen concentration-depth profile is measured by chemical surface analysis, recorded and plotted. The oxygen concentration is low and its peak is below about 200 Angstroms when the fire causes the short because the melt bead was formed in a relatively oxygen poor ambient atmosphere. The oxygen concentration is higher and peaks between 200 and 2000 Angstroms when the short causes the fire because the melt bead was formed in a relatively oxygen rich ambient atmosphere. The oxygen concentration is still greater and remains high to a substantially greater depth of, for example, 20,000 to 40,000 Angstroms, when the conductor had been subjected to an overload current for a substantial time period.

12 Claims, 8 Drawing Figures

A – SHORT CIRCUIT CAUSED BY FIRE

B – FIRE CAUSED BY SHORT CIRCUIT

C – OVERLOAD CONDITION

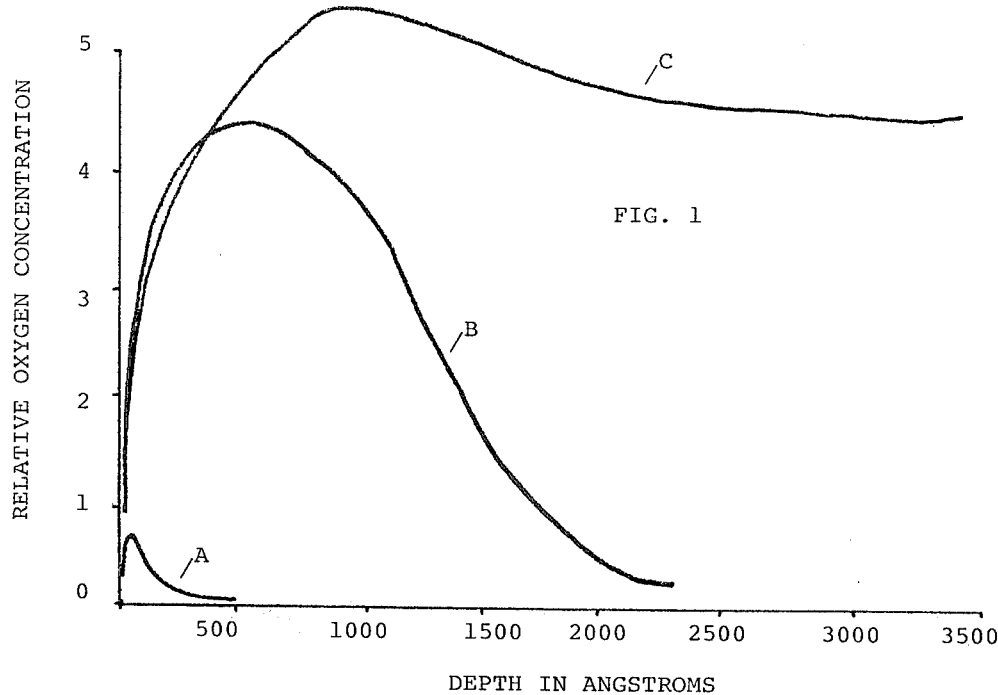
A — SHORT CIRCUIT CAUSED BY FIRE
B — FIRE CAUSED BY SHORT CIRCUIT
C — OVERLOAD CONDITION
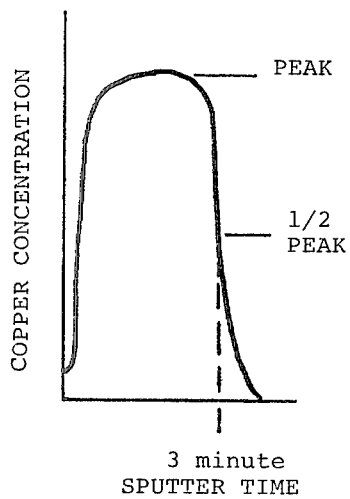
FIG. 2
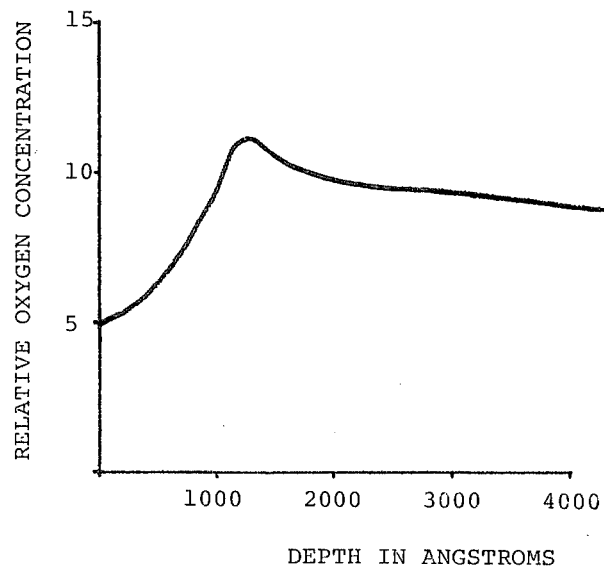
FIG. 3

METHODS FOR USE IN FIRE INVESTIGATION

TECHNICAL FIELD

This invention relates to testing methods and analysis as an aid in determining the origin or cause of a fire in a vehicle, building structure or the like. More particularly, the invention relates to the selection and chemical analysis of portions of electrical wiring or other electrically conductive materials which exhibit signs of having melted at the time of the fire.

BACKGROUND ART

The investigation of a destructive fire to find its cause is necessary in order to determine whether there should be any civil liability due to defective products or workmanship and to determine whether the fire was caused by arson.

Through education, training and experience many individuals are able to inspect a fire scene and, based on fire patterns and other evidence observed at the scene, form an expert opinion on the cause and origin of the fire.

However, electrical malfunctions pose particularly difficult problems for an investigator because the extrinsic evidence looks the same whether a short circuit caused or was caused by a fire. For example, a staple through a Romex cable, an overloaded circuit or poorly installed conductors can cause an overload or overcurrent in the wires and, over a long period of time result in a breakdown of the insulation. Eventually, the conductors may come into contact with each other and short circuit.

Similarly, however, a raging fire or a fire from a trash can, cooking stove or the like, may itself destroy the insulating and subsequently result in an electrically similar short circuit having the same appearance.

A short circuit caused in either manner is usually apparent from the presence of melt beads or melted sections along the copper or aluminum conductors. Until now, it has been difficult and usually is impossible to determine whether these short circuits were caused by or caused the fire. Where, in the past, other evidence strongly suggested that the short circuit did not cause the fire, it was still impossible for the expert investigator to rule out on the basis of a laboratory test or analysis, for example in court room testimony, the possibility that the short circuit had caused the fire.

BRIEF DISCLOSURE OF THE INVENTION

The invention is based on the theory that a short circuit in electrical wiring or other electrically induced melting of a conductive material if it causes a fire will occur in an ambient atmosphere which has a relatively abundant oxygen supply. Thus, in most building structure or vehicle fires in which a short circuit causes the fire, the short would occur in the ordinary atmospheric gas composition which contains approximately 20% oxygen.

However, if the short circuit is caused by the fire, the ambient atmosphere at the time of the short circuit would have relatively little free oxygen due to the fact that large quantities of oxygen are being consumed by the surrounding combustion. Therefore, the oxygen concentration in the melt beads would be relatively different if the short occurred in a relatively oxygen rich atmosphere than if the short occurred in a relatively oxygen poor atmosphere.

Copper or aluminum conductors as manufactured contain only trace amounts of oxygen. Older conductors which have been installed for some time often exhibit some corrosion and therefore may have some surface oxygen combined with the copper or aluminum to form an oxide. However, this oxygen is usually present in a thin surface layer and only to a depth of approximately 50 angstroms. Beneath this surface oxidation, the wire is in substantially the same form and chemical composition as it was immediately after it was originally manufactured.

We have found that a reliable indicator of the conditions under which a short circuit occurred is an oxygen concentration-depth profile. Such a concentration-depth profile is obtained by measuring the relative oxygen concentration at a plurality of depths by the use of modern, chemical, surface analysis techniques.

The invention is essentially a method for testing whether an excessively high electrical current caused or was caused by a fire. The method comprises the steps of first selecting from the region of a fire a specimen which is an electrical conductor having a portion which has been melted after its original manufacture and secondly measuring and recording the relative oxygen concentration at a plurality of depths below the surface of the melted portion. Preferably, the oxygen concentration is plotted on a graph as a function of depth below the surface to give an oxygen concentration-depth profile.

The method further contemplates measuring the depth beneath the surface of a melt bead at which the relative oxygen concentration reaches a peak. It further contemplates measuring the magnitude of the peak of the relative oxygen concentration below the surface of the melt bead. As a further embodiment, a cross-sectional surface through the bead may be exposed and analyzed by a line scan, spectroscopy, surface analysis to measure the relative oxygen concentration across the cross-sectional surface. This indicates whether a remelt of a melt bead has occurred.

The method of the invention may be applied not only to shorted electrical conductors but also to other melted conductive materials to determine whether their melting occurred at the initiation of a fire or after it began. This would apply, for example, in a situation where electrical conductors may have fallen upon a grounded metallic plumbing appliance such as a bathtub.

In performing the methods of the present invention, both the magnitude of the oxygen concentration at various levels beneath the surface of the melted conductive material as well as the depth to which the oxygen has migrated are significant.

Generally, we have found that, in the case where a fire causes a short circuit, the oxygen concentration-depth profile exhibits the characteristics that relatively little oxygen is found in the surface of a melt bead and further that the oxygen concentration falls off relatively rapidly toward the interior of the wire. We have found, for example, that, in a typical case, oxygen concentration peaks at a depth of 200 angstroms or less and thereafter diminishes relatively rapidly.

Therefore, in the case where a fire causes a short circuit which therefore occurs in an oxygen poor atmosphere, the oxygen concentration-depth profile has a relatively low peak oxygen concentration which occurs less than about 200 angstroms below the surface and the oxygen concentration falls off rapidly.

In the circumstances where the short circuit causes a fire, so that the short circuit occurred in a relatively oxygen rich atmosphere, we have found that the oxygen concentration-depth profile is characterized by there being more oxygen, a higher oxygen concentration peak, the oxygen extending deeper into the surface of the conductive material, and the oxygen concentration falling off slower, that is, with a lesser gradient.

For example, in a typical case the oxygen concentration-depth profile will peak at a depth from about 200 angstroms to 2,000 angstroms and thereafter fall off very slowly.

In a third situation, an electrical conductor may be subjected to an overcurrent for a long period of time as a result of an electrical overload. In such a situation, the conductor may be heated for many hours or days prior to the occurrence of any fire. We have found that the oxygen concentration is considerably more than in either of the first two situations and extends to a considerably greater depth. In this situation the peak oxygen concentration will not only be greater but the oxygen will extend considerably further into the interior of the conductive material, for example, to a depth of 20,000 to 40,000 angstroms. Thus, the oxygen concentration-depth profile for the overcurrent situation is characterized by a rapid increase to a high peak and a levelling off at a value near the peak which extends to a considerably greater depth than occurs in the first two situations.

BRIEF DESCRIPTION OF THE DRAWINGS

FIG. 1 is a graph illustrating typical oxygen concentration-depth profile curves for the above three conditions which is based on experimental data.

FIG. 2 is a graph illustrating a method for calibrating the etching rate of a chemical surface analysis instrument.

FIGS. 3–6 are graphs illustrating data for several particular examples of the present invention.

BEST MODE FOR CARRYING OUT THE INVENTION

Figure 4:
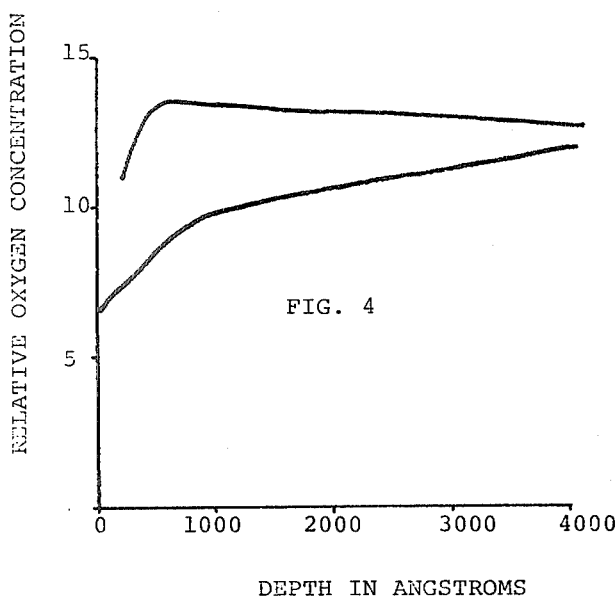

In inspecting a fire scene, an investigator may find one or several places at which electrical wiring has been severed as shown by ends of bare wires drooping down. On the ends or sides of some of these wires there may be melt beads which indicate that a portion of the metal from which the wire is fabricated, was melted and may have splattered off. Such melt beads usually, though not always, have a generally convex spherical, surface which is characteristic of drops of liquid.

In performing the method of the present invention the investigator should preferably select as a specimen, pieces of wire having melt beads which are relatively symmetrical and have small surface areas which are sufficiently smooth to permit analysis by surface spectroscopy. A bead surface which appears smooth at a magnification in the range of 10× to 20× is deemed to be sufficiently smooth.

The investigator may select a few samples from each occurrence of an apparent short circuit, selecting those melt bead samples on the basis of the above criteria.

The selected specimens are then analyzed and measured to obtain an oxygen concentration-depth profile by means of chemical surface analysis. Methods and procedures for performing a chemical surface analysis of metals are known in the prior art and apparatus for use in performing this measurement is commercially available. The inventors are presently aware of five companies from which these are available and the companies are: Physical Electronics Industries, Inc., of Eden Prairie, Minn.; Varian Associates of Palo Alto, Calif.; Inficon (Leybold-Heraeus) East Syracuse, N.Y.; GCA/McPherson Instrument Company, Acton, Mass.; and 3M Company of St. Paul, Minn.

In these methods, the surface of the specimen, such as a melt bead surface, is irradiated with atomic particles causing atomic particles from the specimen to be ejected. The energy of the ejected particles is then detected and is indicative of the elemental composition of the specimen.

Currently there are three systems for surface analysis known in the prior art and these are: ESCA, which is electron spectroscopy for chemical analysis; AES, which is Auger electron spectroscopy; and SIMS, which represents secondary ion mass spectrometer.

We prefer the use of Auger spectroscopy in which a specimen is excited with an electron beam causing inner shell electrons to be removed from the atoms present in the specimen through a relaxation mechanism. Outer shell electrons fill the created vacancies and so-called "Auger electrons" are ejected from the material and an "Auger spectrum" is obtained by plotting the derivative of the electron energy distribution vs. energy.

The electron beam which bombards the surface is scanned across the surface and as this occurs the surface is etched off layer by layer. Therefore, as time progresses the specimen composition is measured at progressively greater depths.

In Auger electron spectroscopy each element present in the specimen has a characteristic energy spectrum. Thus, the number of electrons emitted from the sample at a particularly energy level indicates the concentration of the particular element in the specimen at the tested depth. Although Auger electron spectroscopy permits analysis of a specimen for a broad variety of elements, the invention contemplates the analysis of the specimen to determine the oxygen concentration at various depths below the surface.

As is known in the prior art of Auger electron spectroscopy, it is advantageous to electronically differentiate the energy distribution of the emitted electrons (i.e., number ejected vs. their energy) with respect to electron energy in order to obtain large sharp peaks which stand out much more sharply and well defined against a relatively flat background. With such differentiation, the relative oxygen concentration is proportional to the peak to peak amplitude of the differentated curve of energy distribution for ejected electrons.

While it is difficult to correlate the peak amplitude of this Auger spectrum to absolute or actual concentration of oxygen in the specimen, the relative concentration at various depths may be determined by comparison of the relative peak amplitudes of the Auger spectrum.

Since the analysis involves the comparison of relative concentrations, it is obviously important that the instrument be operated under the same conditions for all testing. For example, if the incident electron beam is one, five or ten KeV for one test, it should be one, five or ten KeV respectively for other tests in order that relative concentrations can be compared.

In testing and measuring specimens in accordance with the present invention, it has been found that contaminating surface elements may have diffused into a thin surface layer of the metal conductor. This surface debris may, for example, be carbon or chlorine and ordinarily is not present below a depth of 25 to 50 angstroms. This is not surprising in view of the fact that polyvinyl chloride is a common insulating material for electrical wiring and carbon is a common product of combustion.

There may also be materials deposited on the surface after the bead hardened. For example, during a fire a bead may drop into ash. This should be washed off prior to analysis.

FIG. 1 graphically illustrates plotted data from three controlled experiments in which the relative oxygen concentration was measured, recorded and plotted as a function of depth below the surface of a selected melt bead for use in visual analysis.

Graph A represents a situation in which a short circuit was caused by a fire. In order to obtain the data for plotting graph A, a section of stove pipe was mounted on top of a screen-covered, three-legged stand with a Bunsen burner beneath the screen. A hole was drilled through the stove pipe and a section of white covered Romex cable was inserted through the hole. The pipe was partially filled with wood and scraps of carpet. The Romex cable was energized at 120 volts and the propane fed Bunsen burner ignited the wood and carpet. A cover was placed over the top of the pipe to try to keep the majority of the smoke within the pipe to simulate actual fire conditions. The fire was allowed to burn until a short circuit occurred.

Graph A illustrates that the relative oxygen concentration at these conditions was substantially less than that for graphs B and C. It fell off very rapidly and became substantially zero at a relatively shallow depth. Because the oxygen concentration curves asympototically approach zero, we select and define the point at which the concentration becomes substantially zero to be the knee of the curve, that is, where the curve begins to level off. In the case of graph A, the curve becomes substantially zero at approximately a depth of 200 angstroms.

Graph B represents a situation in which the fire was caused by a short circuit. To obtain this data, a second sample was prepared by removing the insulation from two copper conductors of the type used in electrical wiring. The opposite ends of the conductors were attached to a 120 volt source with a 20 ampere electrical fuse. The copper wires were then preheated with a propane torch for 15 seconds and physically brought together into contact. The preheating simulated the preheating which usually occurs in a typical wiring failure in which a short begins as a leakage current through a high resistance. With time and deterioration, the current increases causing more power dissipation in the short. The beads from this second experiment were then analyzed by Auger electron spectroscopy and the resulting data was plotted as graph B.

The peak oxygen concentration of graph B was considerably greater than that for graph A and occurred at about 500 angstroms. The oxygen concentration fell to substantially zero at a depth of between 1500 and 2000 angstroms. Furthermore, the concentration gradient at a depth greater than the peak for graph B was less than that for graph A because the concentration fell off more gradually.

Graph C of FIG. 1 represents an overload or overcurrent condition. To obtain the data of graph C, a third sample was prepared by short circuiting a 3 KVA stepdown transformer with a 10 to 1 turns ratio with a completely bared copper conductor from which all of the insulation had been removed. The primary of the transformer was connected to a variable voltage supply. The primary current was increased until the secondary current reached a value of 150 amperes. This overcurrent condition heated the copper conductor until the conductor eventually separated.

A melt bead, formed at the point of separation, was then analyzed by Auger electron spectroscopy. The relative oxygen concentration as a function of depth was plotted as graph C.

From graph C it can be seen that the peak relative oxygen concentration occurred at about 1000 angstroms and was considerably greater than the peak oxygen concentration for either graph A or graph B. Furthermore, the oxygen concentration remained relatively high to a relatively greater depth into the interior of the analyzed melt bead.

In applying Auger electron spectroscopy to the methods of the present invention, it is necessary to calibrate the Auger electron spectroscopy instrument so that the measured data can be correlated with depth below the surface of the specimen. In performing the measurement, the specimen is bombarded with electrons for a period of time during which the surface is etched away as the ejected electron energies are being measured. It is therefore necessary to correlate the time during which bombardment occurs, referred to as sputter time, to the depth achieved. As time progresses surface layers are removed to an increasingly greater depth.

To perform this calibration, a gold substrate was electrodeposited with a layer of copper of precise, known thickness.

The copper surface was then exposed to Auger electron spectroscopy and the time measured from the beginning of the bombardment until the appearance of the element gold in the measured data. Assuming that the etching is a linear function of time, a conversion factor can then be determined to convert electron bombardment or sputter time to the depth at which the oxygen concentration is being measured. In this manner the etching rate can be calculated.

For example, if the copper layer on the gold substrate is 300 angstroms thick and if the element copper disappeared in the Auger spectrum after 3 minutes of sputter time, it can then be calculated that the electron beam etches the surfaces at a rate of 100 angstroms per minute.

FIG. 2 is a graphical plot of a typical curve showing copper concentration as a function of sputter time for such a copper-on-gold standard. Since the curve has no discontinuous changes in oxygen concentration, the actual sputter time is defined as the time at which the copper concentration curve falls to one-half its peak value.

In a fire situation it is possible that a melt bead could be created by a short circuit in the wiring and that thereafter the intense heat of the fire would further melt the copper of the wiring and cause it to cover and solidify over the initial melt bead. If this occurred, the results of the above methods would be invalid. In order to determine whether or not such a remelt has occurred, the melt bead, after being tested as above, can have a portion removed to expose a cross-sectional surface through the melt bead.

A line scan, Auger electron spectroscopy analysis, can then be performed across this exposed surface. With such a line scan, the impinging electron beam is not scanned over a surface but rather is scanned along a line from one edge of the exposed surface to the other. The results provide an indication of the oxygen concentration profile from one surface of the melt bead to the opposite surface.

Figure 7:
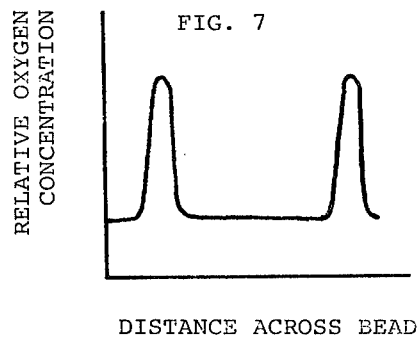
FIGS. 7 and 8 illustrate oxygen concentration-depth profiles obtained by line scans across a cross-section of a melt bead to determine whether a remelt has occurred.

Referring to FIG. 7, if the line scan analysis shows two spaced regions of relatively high oxygen concentration separated by an interior central region of essentially no oxygen, it can be concluded that the interior of the melt bead is chemically identical to the interior of the copper conductor as it was manufactured and therefore no remelt occurred.

Figure 8:
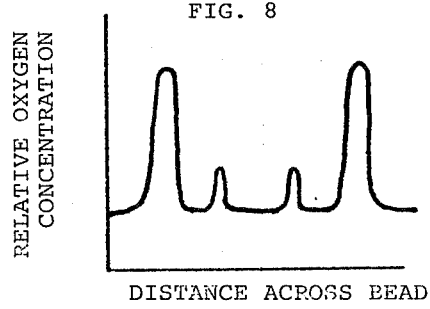

However, referring to FIG. 8, a line scan may show a pair of interior regions of significant oxygen concentration. The two small interior peaks of oxygen suggest that a remelt occurred. The position of these two small inner peaks are the positions of the surfaces of the initial melt bead which later was covered by melted copper, the surface of which was further oxidized.

Therefore, the absence of such interior oxygen concentration peaks shows that there has been no remelt.

EXAMPLES

Six specimens were tested from actual fire investigations.

EXAMPLE I

A length of stranded copper wire approximately 14 centimeters in length, with a melt bead on one end was taken from a portion of the power cord from a small electrical toaster. There was no doubt from other evidence at the fire scene that the small kitchen fire which resulted originated at the toaster.

The sample was tested in the manner described above and the measurements are plotted in FIG. 3.

Because the oxygen concentration-depth profile plotted in FIG. 3 rose to a peak, fell and began levelling off at a depth greater than 200 angstroms but less than 2000 angstroms, the test confirmed that the short circuit occurred in an oxygen rich atmosphere and therefore was the cause of the fire. The relatively high level to which the oxygen concentration fell and was maintained to substantially greater depths suggests that some overcurrent heating of the wiring may have occurred prior to the short circuit which caused the fire.

EXAMPLE II

A copper conductor in a branch circuit in a small utility room was selected having melt beads. The melt beads and a surface of the conductor 1 inch away from the melt bead were both measured in the manner described above.

The data from this measurement is plotted in FIG. 4 and shows that the oxygen concentration rose to substantial peaks and levelled off remaining high for very substantial depths into the conductor. This indicates, as confirmed by other evidence at the fire, that the problem lie with a faulty circuit breaker which allowed an extensive overcurrent condition.

EXAMPLE III

Figure 5:
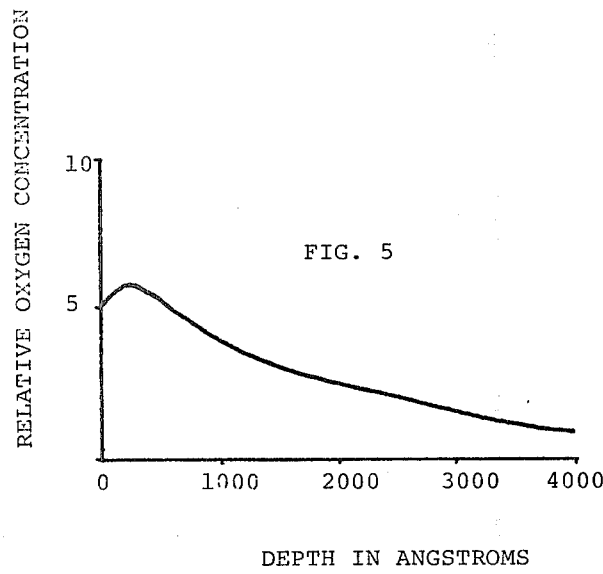

A control conductor having a melt bead was removed from an automatic coffee maker which had been present in a fire. The melt bead was analyzed in accordance with the methods described above and the data is plotted in FIG. 5. The occurrence of the peak oxygen concentration at substantially 200 angstroms and its relatively rapid decrease thereafter indicates that the short circuit was caused by fire.

EXAMPLE IV

A copper conductor from an attic involved in a fire and having a melt bead was selected and measured in accordance with the above described methods. The results of that measurement is plotted in FIG. 6.

Figure 6:
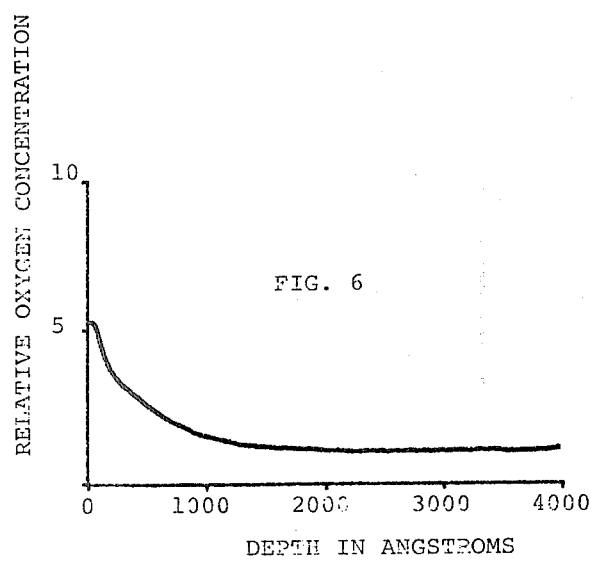

The graph of FIG. 6 illustrates that the peak oxygen concentration occurs substantially below 200 angstroms and that the curve has begun to level off by a depth of about 200 angstroms. This therefore indicates that the short circuit involved did not cause the fire but rather occurred while the fire was in progress.

We claim:

1. A method for testing for whether an excessively high electrical current caused or was caused by a fire, said method comprising:
    (a) selecting from the region of said fire a specimen which is an electrical conductor having a portion which has been melted after original manufacture; and
    (b) measuring and recording the relative oxygen concentration at a plurality of depths below the surface of said melted portion.

2. A method in accordance with claim 1 wherein said melted portion is a melt bead having a region of relatively smooth surface.

3. A method in accordance with claim 2 wherein said beaded specimen is a severed end of a piece of electrical wiring.

4. A method in accordance with claim 1 or claim 3 further comprising plotting a graph of said relative oxygen concentration as a function of depth for use in visual analysis.

5. A method in accordance with claim 1 wherein said measuring is accomplished by Auger electron spectroscopy.

6. A method in accordance with claim 1 wherein said measuring is accomplished by electron spectroscopy for chemical analysis.

7. A method in accordance with claim 1 wherein said measuring is accomplished by secondary ion mass spectrometry.

8. A method in accordance with claim 1 wherein said method further comprises measuring the depth at which the relative oxygen concentration is at a peak.

9. A method in accordance with claim 1 wherein said measuring and recording steps further comprise the steps of:
    (a) exposing a cross-sectional surface through said portion; and
    (b) measured by a line scan, spectroscopic, surface analysis, the relative oxygen concentration across said cross-sectional surface.

10. A method for determining whether an electrical wiring short circuit in the vicinity of a fire caused or was caused by the fire, said method comprising:
    (a) selecting a melt bead formed of electrical wiring material located at the short circuit; and
    (b) measuring the depth at which the relative oxygen concentration below the surface of said melt bead reaches a peak; whereby the occurrence of said depth at least than substantially 200 angstroms is indicative of the short being caused by the fire and the occurrence of said depth at greater than substantially 200 angstroms and less than substantially 2000 angstroms is indicative of the short being the cause of the fire.

11. A method in accordance with claim 10 wherein said method further comprises measuring the peak relative oxygen concentration beneath said surface.

12. A method for determining whether an electrical wiring short circuit in the vicinity of a fire caused or was caused by the fire, said method comprising:
 (a) selecting a melt bead formed of electrical wiring material located at the short circuit; and
 (b) measuring the peak relative oxygen concentration below the surface of said melt bead.

* * * * *